United States Patent [19]
Simmons, Sr.

[11] Patent Number: 5,748,278
[45] Date of Patent: May 5, 1998

[54] EYEGLASS SHIELD FOR REMOVABLE ATTACHMENT TO EYEGLASS LENS FRAMES

[75] Inventor: Bennie F. Simmons, Sr., Lewisville, Tex.

[73] Assignee: Safety Optical Service Company, Lewisville, Tex.

[21] Appl. No.: 695,088

[22] Filed: Aug. 8, 1996

[51] Int. Cl.$^6$ ............................... G02C 7/10; A61F 9/02
[52] U.S. Cl. .................................. 351/44; 2/449
[58] Field of Search ........................... 351/44, 47, 111, 351/121, 140, 158; 2/448, 449, 451, 12, 13

[56] References Cited

U.S. PATENT DOCUMENTS 5,608,469  3/1997  Bollé ........................................ 351/44

OTHER PUBLICATIONS

Information sheet for Top–Side I–Guard, printed 1964–1967. No month.
Information sheet for Templeclip, date unknown.
Invoice of Gateway Amsafe for Universal Side Shield, 1993. No month.
Sample of Gateway Amsafe Universal Side Shield, 1993. No month.
Sample of Safety Optical Services Side Shield, Part No. 52. No date.
Titmus Distributor Price List/Catalog, printed 1994. No month.

Primary Examiner—Huy Mai
Attorney, Agent, or Firm—Jones, Day, Reavis & Pogue

[57] ABSTRACT

A full sideshield for removable attachment to each side of an eyeglass frame having a pair of eyeglass lens holding frames and a pair of pivotal temple for holding said eyeglass lens holding frames on the head of a user to provide at least partial eye protection on the top, bottom, and side of the eye. The sideshields are attached to the eyeglass lens holding frames in a detachable manner and are mounted such that they do not interfere with movement of the eyeglass temples so that the temples can be folded or, if they are spring pivoted temples, can move outwardly a predetermined amount without substantial interference by the sideshields.

15 Claims, 3 Drawing Sheets

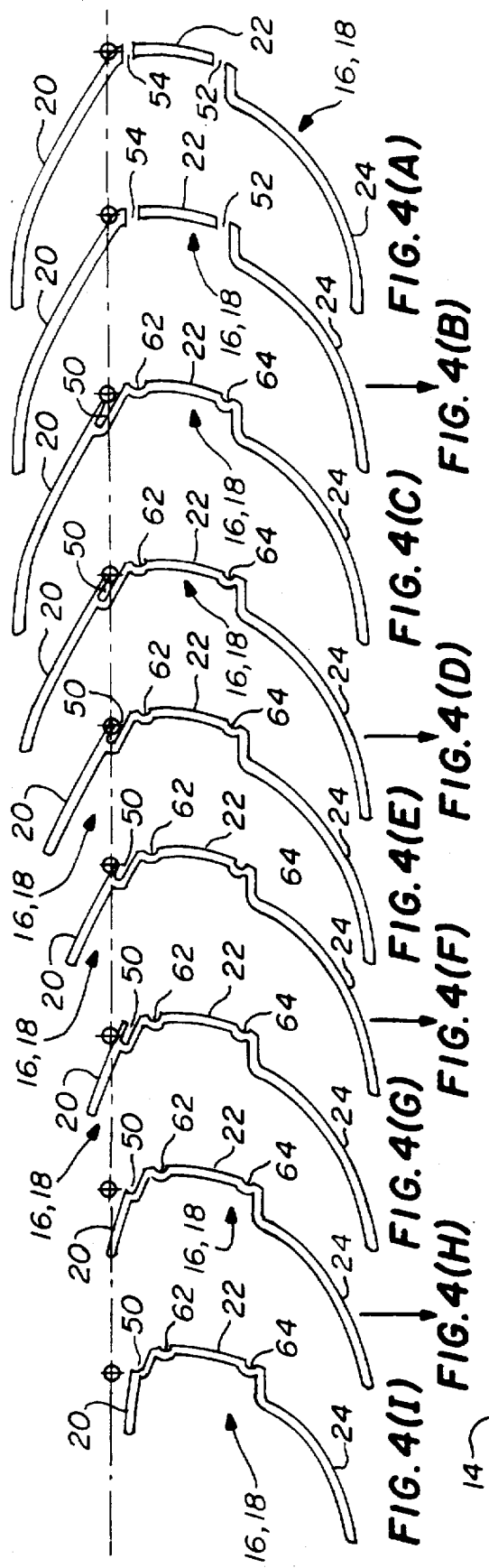
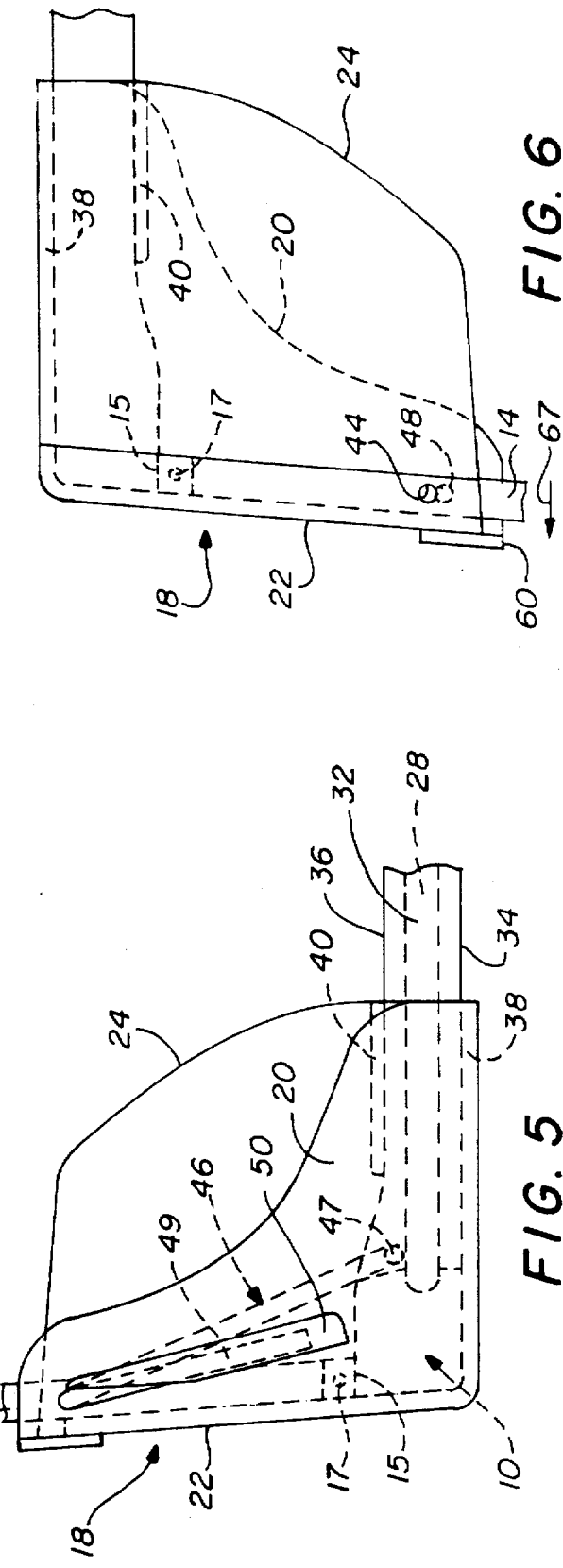

EYEGLASS SHIELD FOR REMOVABLE ATTACHMENT TO EYEGLASS LENS FRAMES

BACKGROUND OF THE INVENTION

1. Field of the Invention

The present invention relates in general to safety glasses to provide protection to the eyes and in particular to a full sideshield for removable attachment to an eyeglass frame without interfering with movement of the eyeglass temples.

2. Description of Related Art Including Information Disclosed Under 37 CFR 1.97 and 1.98

Safety glasses are well known in the prior art and are used to protect the eyes of an individual from airborne particles, high-velocity projectiles, wind, and the like.

There are many different types of eye shields that are used with eyeglass frames. Some are permanently attached to the eyeglass frames and provide reasonable protection for the top, side, and bottom of the eye. Others simply provide limited protection to the eye from the side thereof with limited protection for the top and the bottom area of the eyeglass frame. When eye shields providing such limited protection fit a broad range of frame shapes and sizes, they are known as universal sideshields and, as stated, provide limited side protection for glasses of all sizes and shapes. An eyeglass frame, as used herein, includes the front portion and temples or bows.

One such type of universal sideshield is of plastic construction having a side flap, partial top and bottom flaps, and front flaps extending from each of the side and top portions that fold around the front edge of the eyeglass frame. The temple of the eyeglass frame on each side is inserted through appropriate slots formed in the side portion of the shield so that the eye shield can slide on the temple toward the eyeglass front and be held in place by the temple. In such case, when the temples are folded, the sideshields move with the temples and thus are subject to repositioning themselves on the temples thus requiring a readjustment each time the temples are folded and then unfolded.

Another type of sideshield includes substantially a clear side portion with a perpendicularly extending top portion and a small perpendicularly extending front portion that engages the front portion of the eyeglass frame. There is a resilient continuous elastic band that passes through four orifices in the side to enable the temples to slide under two spaced portions of the continuous elastic band to hold the shield to the temple of the glasses. Again, each time the temples are folded, the sideshield moves with the temples thus causing readjustment to be necessary each time the temples are folded and unfolded. Also, this sideshield provides very little protection for the top of the eye and none from the bottom.

A third type of universal eye shield is attached to the temple portion of the frame using a screw and nut that clamps the sideshield to the temple when tightened.

Another type of universal eye shield is formed of an injection molded flat part that has four slots at different points through which the temple of the eyeglass frame can be threaded and attempt to adjust for pantoscopic angle variations.

Thus, all known prior art shields are attached to the temples and move with the temples except those which are permanently attached to the eyeglass front.

Further, each of the known detachable sideshields has molded into them a fixed pantoscopic angle (the angle the temple makes with the eyeglass front to which it is attached) that cannot be easily varied for glasses with a different pantoscopic angle.

It would be desirable to have a full sideshield to provide substantial protection for the eye from the top, side, and bottom and which would fit a broader range of eyeglass frames than most sideshields, that could be quickly and simply attached to the broad range of size and type of eyeglass frames and that could be quickly and removably attached to the eyeglass frames themselves instead of the temples. In such case, the pantoscopic angle of the eyeglass frame is unimportant whereas it is important when the shield is attached to the temple.

SUMMARY OF THE INVENTION

As used herein, the terms "eye shield" or "sideshield" are synonymous and are used interchangeably. The present invention provides a full sideshield for removable attachment to an eyeglass frame without interfering with movement of the temples attached to the eyeglass frame. The sideshield is generally arcuate shaped having a periphery for generally conforming to the shape of the eyeglass frame and has a top portion, a bottom portion, and a side portion integrally formed as a single unit. First and second spaced flange portions extend respectively inwardly from the eye shield at least partially in front of and substantially parallel to the eyeglass frame and at least partially behind and substantially parallel to the eyeglass frame to secure the eyeglass frame between the first and second flange portions. A resilient, detachable fastener securely attaches the sideshield to the eyeglass frame hinge itself without interfering with movement of the temples.

Thus it is an object of the present invention to provide a full sideshield for removable attachment to an eyeglass frame without interfering with movement of the temples attached to the eyeglass frame.

It is another object of the present invention to provide a substantially full sideshield for removable attachment to an eyeglass frame that makes the pantoscopic angle of the pair of temples of the eyeglasses unimportant.

It is still another object of the present invention to provide a full sideshield for removable attachment to an eyeglass frame than can be quickly and simply attached to a broad range of size and type of eyeglass frames.

It is yet another object of the present invention to provide a full sideshield for removable attachment to an eyeglass frame utilizing either a spring clip, a resilient O-ring, or a combination of the spring clip and O-ring.

It is still another object of the present invention to provide a full sideshield for removable attachment to an eyeglass frame that allows a temple to move outwardly a predetermined amount such as five degrees on a spring hinge.

Thus the present invention relates to a full sideshield for removable attachment to each side of an eyeglass frame having a pair of lens and a pair of pivotable temples for holding the eyeglass frames on the head of a user to provide at least partial eye protection on the top, bottom, and side of the eye. The eye shield comprises a generally arcuate-shaped sideshield removably attached to each frame front in a fixed relationship and having a periphery generally conforming to the frame front. Each sideshield has an integrally formed top portion, side portion, and bottom portion for protecting the eyes of the user. A resilient detachable fastener releasably engages both the eyeglass frame front hinge and the sideshield to removably attach the eye shield to the lens frame in a fixed relationship without interfering with pivotal movement of the temples. The resilient detachable fastener may be a resilient metal fastener mounted on the eye shield and having a first portion on one side of the eye shield for engaging the glass frame temple mounting bracket hinge or projection and a second portion on the other side of the eye shield. A recessed slot in the other side of the eye shield is located such that the second portion of the fastener is resiliently deformed when removably placed in the slot so as to cause the full eye shield to be tightly held to the eyeglass frame front.

In another embodiment, a continuous elastic band engages the temple mounting bracket hinge or projection on the eyeglass frame and extends into first and second spaced slots on the outside surface of the eye shield and along corresponding ones of first and second grooves into third and fourth spaced slots and under a substantially U-shaped eye shield flange such that, by stretching the continuous elastic band to engage the third and fourth slots and pass under the eye shield flange, a tension is applied to the eyeglass frame front and the eye shield to fixedly hold the eyeglass shield to the eyeglass frame front. Both the continuous elastic band and the substantially U-shaped elongated resilient clip or metal fastener may be used simultaneously to securely and detachably attach the full sideshield to the eyeglass frame.

BRIEF DESCRIPTION OF THE DRAWINGS

These and other features of the present invention will be more fully disclosed when taken in conjunction with the following DETAILED DESCRIPTION OF THE PREFERRED EMBODIMENTS in which like numerals represent like elements and in which:

FIGS. 4(A–I) illustrate the cross-sectional views taken along the section lines shown in FIG. 3;

FIG. 5 is a top view of one of the novel sideshields of the present invention shown using a spring clip to attach the sideshield to the eyeglass frame front;

FIG. 6 is a bottom view of the novel eye shield of the present invention illustrating the eye protection received from the bottom of the eye;

DETAILED DESCRIPTION OF THE PREFERRED EMBODIMENTS

Figure 1:
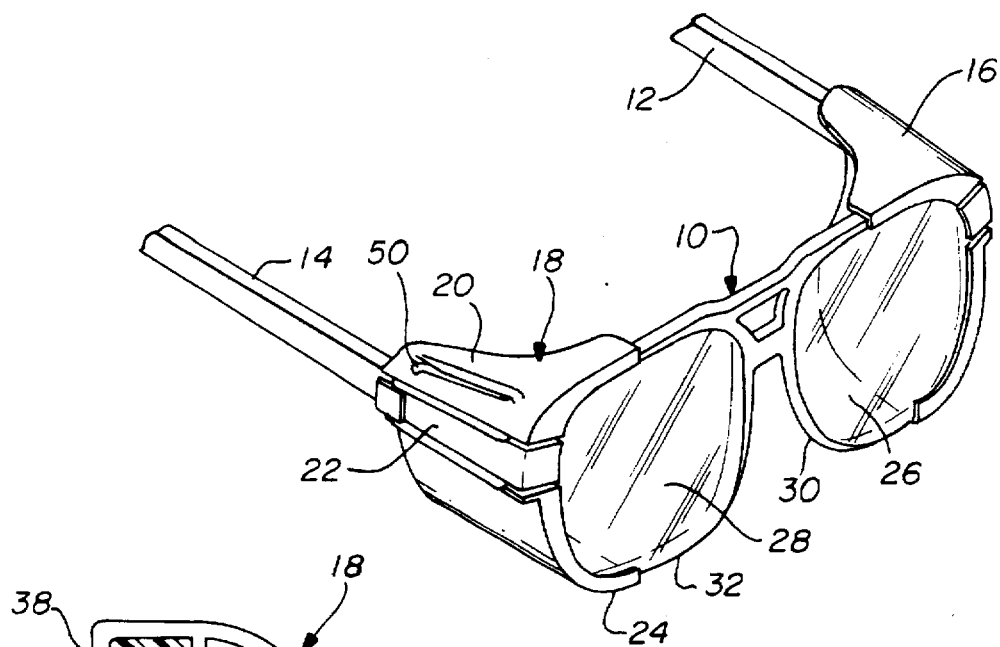
FIG. 1 is a partial isometric view of a pair of eyeglass frames and temples having the novel sideshields of the present invention attached thereto.

FIG. 1 is partial isometric of a pair of eyeglasses having the novel full sideshields removably attached to each side thereof. As can be seen in FIG. 1, the eyeglass frame front portion 10 has temples 12 and 14 pivotally attached to each side thereof for holding the eyeglass frame front 10 on the face of a user. The novel full sideshields 16 and 18 are removably attached on each side of the frame front 10 forming a semicircle around the eyeglass lens 26 and 28 in front of the eye cavity of the user to provide at least partial eye protection on the top, bottom, and side of the eye. Each sideshield 16 and 18 is a generally arcuate-shaped shield having a periphery for generally conforming to the shape of the individual eyeglass lens holders 30 and 32. Each of the novel sideshields 16 and 18 has a top portion 20, a bottom portion 24, and a side portion 22 integrally formed as a single unit.

Figure 2:
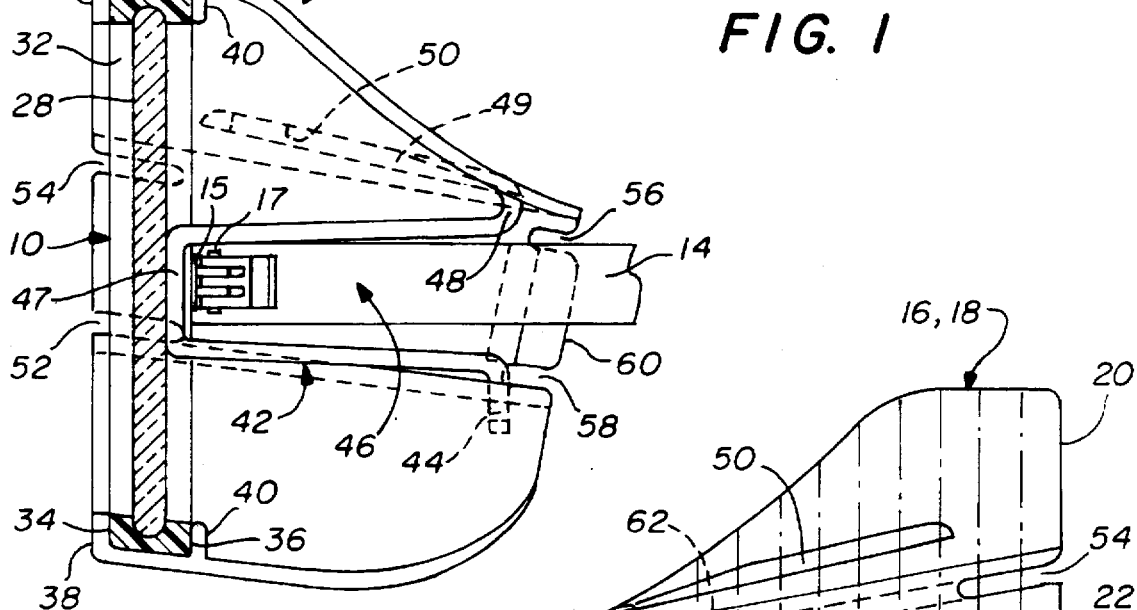
FIG. 2 is an inside view of an eye shield attached to the eyeglass frame, shown in cross-section, and with one of the temples extending outwardly therefrom.

As best can be seen in FIG. 2, a first flange portion 38 extends from the sideshield 18 at least partially in front of and substantially parallel to the eyeglass lens holder 32. A second flange portion 40 extends inwardly from the sideshield 18 at least partially behind and substantially parallel to the eyeglass lens holder 32 to secure the eyeglass lens holder 32 between the first and second flange portions 38 and 40. It will be noted that the first flange portion 38 extends inwardly along the front portion 34 of the lens holder 32 while the second flange portion 40 extends at least partially behind and substantially parallel to the rear portion 36 of the individual eyeglass lens holder 32 thus securing the eyeglass lens holder 32 between the first and second flange portions 38 and 40. This is shown clearly in FIGS. 2 and 5.

Continuing with FIG. 2, it can be seen that temple 14 is hingedly attached to a mounting bracket projection 15 that extends from each side of the individual eyeglass lens holders 30 and 32 for holding the eyeglass frame 10 on the head of the user. The temple 14 is pivotally attached to projection 15 at pivot point 17 as is well known in the art.

Figure 7:
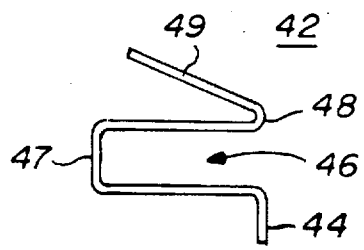
FIG. 7 is a side view of the resilient metal fastener in the form of a substantially U-shaped elongated resilient clip that is used to attach the full sideshield to the eyeglass frame.
Figure 8:
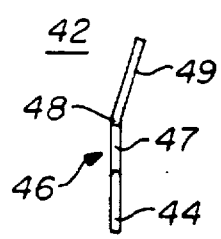
FIG. 8 is an end view of the resilient metal fastener shown in FIG. 7.
Figure 9:
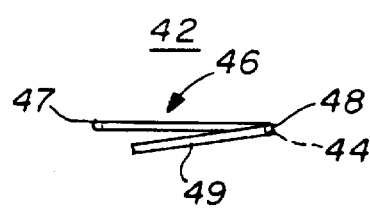
FIG. 9 is a top view of the resilient fastener shown in FIG. 7.

It will be noted in FIG. 2 that the resilient detachable fastener for securely attaching the sideshield 18 to the individual eyeglass lens holder 32 is a resilient metal fastener 42, shown more clearly in FIGS. 7, 8, and 9. The manner in which the resilient metal fastener 42 attaches the sideshield to the eyeglass lens holder 32 is most clearly shown in FIG. 2 and FIG. 5. As can be seen in both FIGS. 2 and 5, the inside surface of the sideshield 18 faces towards the eyeglass lens holder 32 and forms one side of the sideshield 18. An outside surface on the sideshield 18 faces away from the eyeglass lens holder 32, as shown in FIG. 1, and forms the other side of the sideshield 18.

A resilient metal fastener in the form of a substantially U-shaped elongated resilient wire clip 42 is mounted on the sideshield 18 and has a substantially U-shaped elongated resilient clip portion 46 on the inside surface of the sideshield 18 for engaging the eyeglass frame temple mounting bracket projection 15. It also has a second portion 49 extending through the sideshield 18 to the outside surface facing away from the eyeglass lens holder 32. A recessed slot 50 is formed in the outside surface of the sideshield 18 and is located such that the second portion 49 of the resilient metal fastener 42 is resiliently deformed when removably placed in the slot 50 so as to cause the full sideshield 18 to be tightly held to the eyeglass lens holder 32.

As stated earlier, the resilient metal fastener has a substantially U-shaped elongated resilient wire clip portion 46 having first and second ends 44 and 48 pivotally mounted on the sideshield 18 from the inside surface thereof and forming the first portion 46, the U-shaped portion, of the metal fastener 42. The second portion of the resilient metal fastener 42 is an elongated resilient arm 49 that extends parallel to the recessed slot 50 and is integrally formed with the first end 48 of the U-shaped resilient clip 46 and forms the second portion of the resilient metal fastener 42 such that, when the elongated resilient arm 49 is resiliently deformed and placed into said recessed slot 50, the base 47 of the U-shaped elongated portion 46 of the resilient wire clip 42 is forced into engagement with the eyeglass frame temple mounting bracket projection or hinge 15 to hold the sideshield 18 in rigid engagement with the eyeglass frame front 10. This may be more clearly seen in FIG. 5 where in phantom lines the base 47 of the U-shaped portion 46 of the resilient metal fastener is shown against the temple mounting bracket projection or hinge 15. Also the elongated resilient arm 49 is shown in the slot 50 on the outside of the eyeglass sideshield 18.

Note in FIG. 2 that the first flange portion 38 of the sideshield 18 extends partially in front of the eyeglass lens holder 32 at 34 along substantially the entire periphery of the eye shield except for slots 52 and 54. Also note in FIG. 5 that the second flange portion 40 extends only from the top and bottom portions of the sideshield 18 behind the eyeglass lens holder at 36 to secure the eyeglass frame between the first and second flange portions 38 and 40 as shown in FIG. 2.

Figure 3:
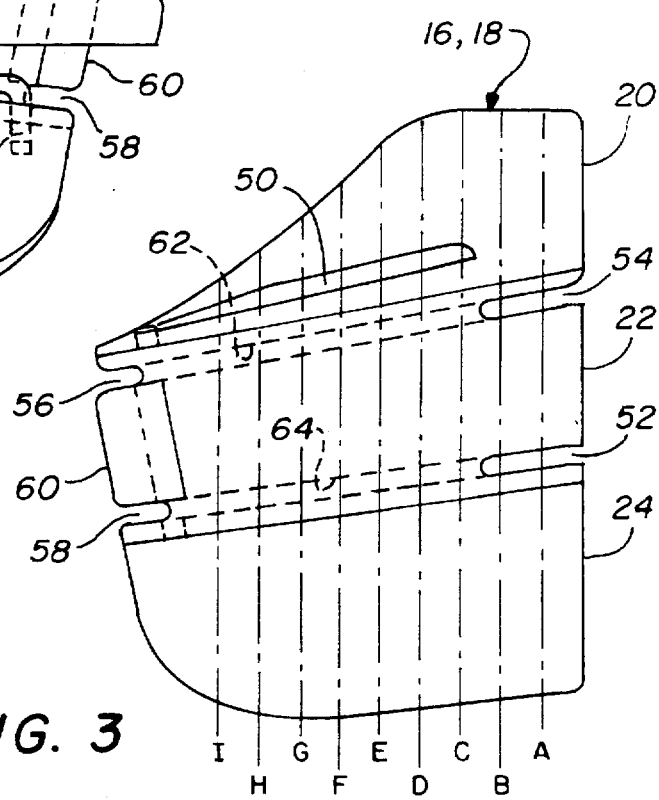
FIG. 3 is a side view of one of the novel eyeglass shields of the present invention illustrating points along which cross-sectional views are shown in FIGS. 4(A–I)

FIG. 3 is a side view of one of the eyeglass sideshields 16 or 18 illustrating various cross-sectional lines through which the cross section is shown in FIGS. 4(A–I). Note again, that the sideshields 16, 18 include a top portion 20, a side portion 22, and a bottom portion 24. A slot 50 is formed in the upper portion 20 for receiving the elongated resilient arm 49 as explained earlier. Further, slots 56 and 58 are formed at the rear of the eyeglass shields 16, 18 for purposes as will be explained hereafter. The slots 56 and 58 form a substantially U-shaped sideshield flange 60. First groove 62 interconnects slots 54 and 56 and second groove 64 interconnects slots 52 and 58.

FIGS. 4(A–I) illustrates the cross-sectional views taken along the lines indicated in FIG. 3 and shows top portion 20, the side portion 22, the bottom portion 24, the slots 52 and 54, the grooves 62 and 64, and the recessed slot 50.

FIG. 6 is a bottom view of the sideshield 18. Because of the flexibility of the eyeglass sideshield 18 and the construction with slots 56 and 58, the temple 14 as illustrated in FIG. 6 can be a spring-loaded temple at hinge 17 as is well known in the art. Thus the temples can move outwardly in a direction away from each other as shown by arrow 67 a predetermined amount such as, for example only, approximately five degrees. Thus, eyeglasses with spring-loaded temples can be accommodated with the present device.

FIGS. 7, 8, and 9 are side views, end views, and top views, respectively, of the novel resilient metal fastener 42. Again, it has a first portion 46 mounted on the inside surface of the sideshield 18 for engaging the glass frame temple mounting bracket projection or hinge 15 at the bottom 47 of the U-shaped portion 46. It has a second elongated resilient arm 49 that is integrally formed with the first end 48 of the U-shaped resilient wire clip or member 46. The entire fastener 42 is mounted in the eyeglass sideshield 16 or 18 by means of orifices therein through which end 44 and end 48 project. Thus the resilient arm 49 is positioned at the outside surface of the sideshield 16 or 18, while the U-shaped portion 46 is on the inside surface of the sideshield 16 or 18. FIG. 8 illustrates the end view and FIG. 9 illustrates the top view of the novel fastener 42.

Figure 10:
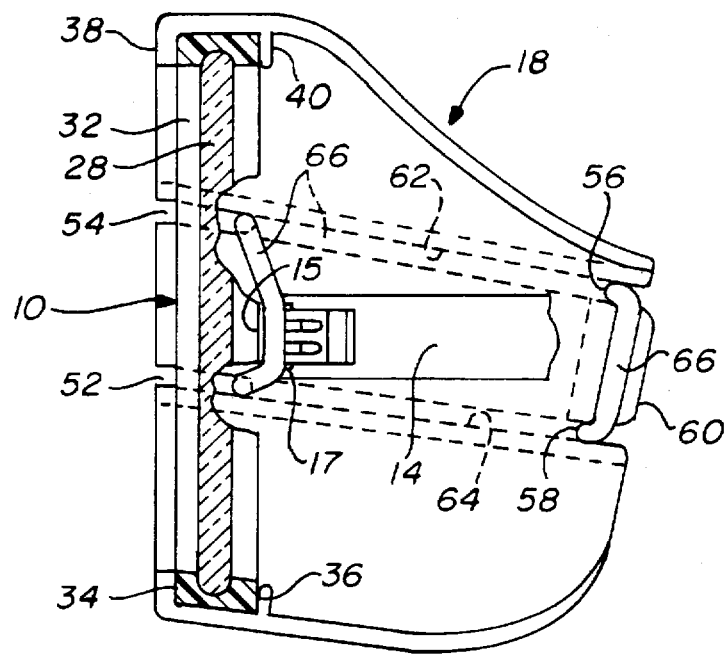
FIG. 10 is a side view of a full sideshield being attached to the eyeglass frame front with a second embodiment utilizing an elongated continuous elastic band.
Figure 11:
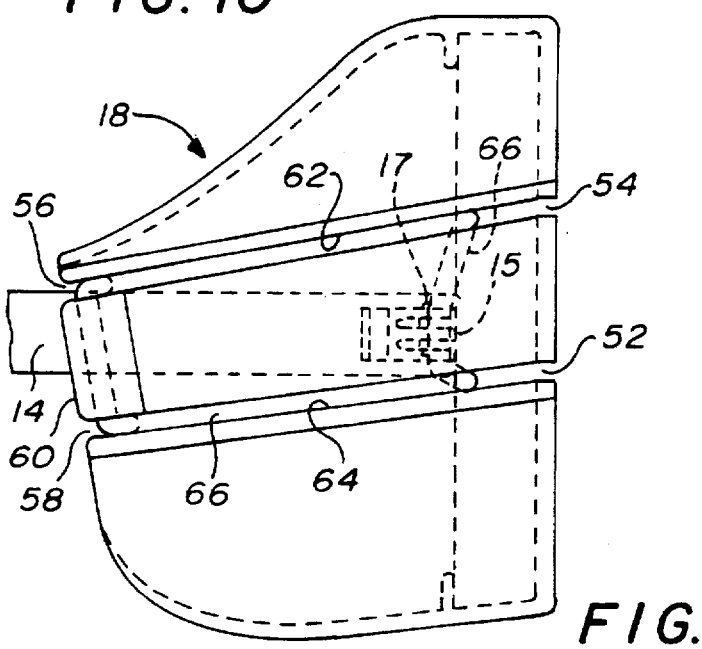
FIG. 11 is an outside view of the full sideshield shown in FIG. 10 illustrating the path followed by the continuously elongated resilient band.

FIGS. 10 and 11 demonstrate a second embodiment of the present invention which could be used either alone or in combination with the first embodiment to hold the sideshield rigidly attached to the eyeglass frame front portion 10. In this embodiment, a continuous elastic band 66, such as, for example only, a rubber O-ring, engages the temple mounting bracket or hinge 15 on the eyeglass frame 10 and extends into the first and second spaced slots 52 and 54 and continues along corresponding ones of the first and second grooves 62 and 64 into the third and fourth slots 56 and 58 and under a substantially U-shaped sideshield flange 60 such that, by stretching the continuous elastic band 66 to engage the third and fourth slots 56 and 58 under the sideshield flange 60, tension is applied to the eyeglass lens holder 32 and the sideshield 18 to fixedly hold the sideshield 18 to the eyeglass lens holder 32. Clearly, this embodiment could be used either alone or in conjunction with the spring-loaded clip 42 as shown in FIG. 2 and FIG. 5.

It can be seen in FIG. 1 that sideshields 16 and 18 are mirror images of each other and thus only one has been disclosed and discussed in detail in FIGS. 2 through 11.

Figure 12:
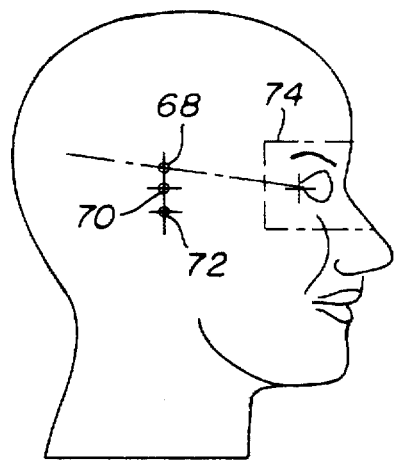
FIG. 12 is a side view of an outline of a human head illustrating in phantom lines the area to be protected by the full sideshield and also illustrating the different pantoscopic angles for various glasses.
Figure 13:
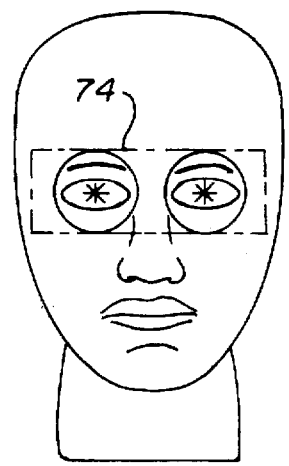
FIG. 13 is a front view of an illustration of a human head showing in phantom lines the area about the eyes to be protected by the full sideshield of the present invention.

FIG. 12 illustrates the different pantoscopic angles that can be found for various eyeglasses. Assuming that the eyeglass front portion 10 is vertically positioned in front of the eye, the temple could extend through either of the points 68, 70, or 72 thus varying the angle between the temple and the eyeglass lens in front of the eye. With the present invention, the pantoscopic angle can change as needed and the temple can extend through any of the points 68, 70, or 72 without affecting the attachment of the sideshield to the eyeglass front portion 10. FIG. 12 also illustrates in phantom lines the area 74 which is desired to be protected by the sideshields. FIG. 13 is a front view of the representation of a face illustrating in phantom lines the area 74 about the eye that is protected by the novel sideshields of the present invention.

Thus there has been disclosed a full sideshield for removable attachment to an eyeglass frame having a front and a back and a pair of pivotally mounted temples attached to corresponding mounting bracket projections or hinges extending from each side of the eyeglass frame for holding the eyeglass frame on the head of a user. The sideshield forms a semicircle around the eyeglass in front of the eye cavity of the user to provide at least partial eye protection on the top, bottom, and side of the eye. The sideshield is generally arcuate shaped and has a periphery for generally conforming to the shape of the eyeglass frame. The sideshield has a top portion, a bottom portion, and a side portion integrally formed as a single unit. First and second flange portions extend at least partially in front of and behind the eyeglass frame front portion to hold the eyeglass frame front portion between the first and second flange portions. A resilient, detachable fastener securely attaches the sideshield to the eyeglass frame without interfering with movement of the temple.

The resilient detachable fastener may be a substantially U-shaped elongated resilient clip having first and second ends pivotally mounted on the sideshield from the inside surface thereof and forming a first portion of the clip. An elongated resilient arm extends parallel to a recessed slot in the outside surface of the sideshield and is integrally formed with the first end of the U-shaped resilient clip and forms a second portion of the resilient clip such that, when the elongated resilient arm is resiliently deformed and placed into the recessed slot, the U-shaped elongated resilient clip is forced into engagement with the eyeglass frame temple mounting bracket projection or hinge to hold the sideshield in rigid engagement with the eyeglass frame. The resilient fastener may also be a continuous elastic band engaging the temple mounting bracket projection or hinge on the eyeglass frame front portion and extending around the temple into first and second spaced slots in the forward end of the sideshield and extending along the outside surface of the sideshield in corresponding ones of first and second grooves into third and fourth spaced slots at the opposite end of the sideshield and then under a substantially U-shaped sideshield flange such that, by stretching the continuous elastic band to engage the third and fourth slots and pass under the sideshield flange, a tension is applied to the eyeglass frame front portion and the sideshield to fixedly hold the eyeglass shield to the eyeglass frame front portion.

Clearly both the substantially U-shaped elongated resilient wire clip and the continuous elastic band could be used in conjunction with each other or separately to hold the sideshield to the eyeglass frame front portion.

The corresponding structures, materials, acts, and equivalents of all means or step plus function elements in the claims below are intended to include any structure, material, or act for performing the function in combination with other claimed elements as specifically claimed.

I claim:

1. A full sideshield for removable attachment to an eyeglass frame front portion having a pair of spaced eyeglass lens holders, the lens holders having a front and a back and a pair of temples attached to a corresponding mounting bracket hinge projection from each side of the lens holder for holding the eyeglass frame on the head of a user, said sideshield having an inside and an outside and forming a semicircle around the eyeglass lens holder in front of an eye cavity of the user to provide at least partial eye protection at the top, bottom, and side of the eye, the sideshield comprising:

- a generally arcuate-shaped sideshield having a periphery for generally conforming to the shape of the eyeglass lens holder and having a top portion, bottom portion, and a side portion integrally formed as a single unit;
- a first flange portion extending from said sideshield at least partially in front of and substantially parallel to said eyeglass lens holder;
- a second flange portion spaced from said first flange portion and extending from said sideshield at least partially behind said eyeglass lens holder and substantially parallel to the first flange portion to secure said eyeglass lens holder between said first and second flange portions; and
- a resilient, detachable fastener for removably attaching each sideshield to a respective eyeglass lens holder in a fixed relationship, without movement, as said temples are moved toward each other.

2. A full eyeglass sideshield as in claim 1 wherein said first flange portion extends from substantially the entire periphery of the sideshield in front of the eyeglass lens holder.

3. A full eyeglass sideshield as in claim 2 wherein said second flange portion extends only from the top and bottom portions of said sideshield behind said eyeglass lens holder and substantially parallel to said first flange portion to secure said eyeglass lens holder between said first and second flange portions.

4. A full eyeglass sideshield as in claim 1 wherein said resilient detachable fastener comprises:

- a resilient metal fastener mounted in said sideshield and having a first portion on the inside of said sideshield for engaging said eyeglass frame temple mounting bracket hinge projection and a second portion on the outside of the sideshield;
- a recessed slot on said outside of the sideshield and located such that the second portion of the fastener is resiliently deformed when removably placed in said slot so as to cause said full sideshield to be tightly held to said eyeglass lens holder without interfering with movement of the temples.

5. An full eyeglass sideshield as in claim 4 further comprising:

- the inside surface of said sideshield facing toward said eyeglass lens holder and forming said inside of said sideshield;
- the outside surface of said sideshield facing away from said eyeglass lens holder and forming said outside of said sideshield;
- a substantially U-shaped elongated resilient wire clip having first and second ends pivotally mounted on said sideshield from the inside surface thereof and forming said first portion of said metal fastener; and
- an elongated resilient arm extending parallel to said recessed slot and being integrally formed with said first end of said U-shaped resilient wire clip and forming said second portion of said resilient metal fastener such that, when the elongated resilient arm is resiliently deformed and placed into said recessed slot, the U-shaped elongated resilient wire clip is forced into engagement with said eyeglass frame temple mounting bracket hinge projection to hold said sideshield in rigid engagement with said eyeglass lens holder.

6. A full eyeglass sideshield as in claim 5 further comprising:

- first and second spaced slots formed in said flange portion end of said side portion of said sideshield;
- third and fourth spaced slots formed in the opposing end of said side portion of said sideshield and forming a substantially U-shaped sideshield flange;
- a first groove connecting said first and third spaced slots;
- a second groove connecting said second and fourth slots; and
- a continuous elastic band engaging said temple mounting bracket hinge projection on said eyeglass lens holder and extending around said temple into said first and second spaced slots and along corresponding ones of said first and second grooves into said third and fourth spaced slots to pass under said substantially U-shaped sideshield flange such that, by stretching said continuous elastic band to engage said third and fourth slots under said sideshield flange, a tension is applied to said eyeglass frame and said sideshield to assist said resilient arm in fixedly holding said eyeglass sideshield on said eyeglass lens holder.

7. A full eyeglass sideshield as in claim 4 further comprising:

- first and second spaced slots formed in said flange portion end of said side portion of said sideshield;

third and fourth spaced slots formed in the opposing ends of each side portion of said sideshield and forming a substantially U-shaped sideshield flange;

a first groove connecting said first and third spaced slots;

a second groove connecting said second and fourth slots; and a continuous elastic band engaging said temple mounting bracket hinge projection on said eyeglass frame lens holder and extending into said first and second spaced slots and along corresponding ones of said first and second grooves into said third and fourth spaced slots and under said substantially U-shaped sideshield flange such that, by stretching said continuous elastic band to engage said third and fourth slots and to pass under said sideshield flange, a tension is applied to said eyeglass frame lens holder and to said sideshield to assist said resilient arm in fixedly holding said eyeglass sideshield to said eyeglass frame lens holder.

8. A full eyeglass sideshield as in claim 4 wherein the eyeglass sideshield for one side of the eyeglass frame lens holder is the mirror image of the other side.

9. A full eyeglass sideshield as in claim 1 wherein:

said pair of temples are attached to said mounting bracket hinge projection in a spring-loaded fashion to enable movement of said temples in a direction away from each other; and said resilient detachable fasteners allows movement of said spring-loaded temples a predetermined distance away from each other.

10. A full sideshield for removable attachment to each side of an eyeglass frame having a pair of eyeglass lens frames and a pair of pivotal temple attached thereto for holding said eyeglass frame on the head of a user to provide at least partial eye protection on the top, bottom, and side of the eye, the sideshield comprising:

a generally arcuate-shaped sideshield removably attached to each lens frame in a fixed relationship and having a periphery generally conforming to the shape of the lens frame;

said sideshield having an integrally formed top portion, side portion, and bottom portion for protecting the eyes of the user; and a resilient detachable fastener for releasably engaging both said eyeglass lens frame and said sideshield to removably attach one of said sideshield to said eyeglass lens frame in a fixed relationship without interfering with pivotal movement of corresponding temples toward each other.

11. A full sideshield as in claim 10 wherein said resilient detachable fastener is a resilient metal clip that engages both said eyeglass lens frame and said sideshield.

12. A full sideshield as in claim 10 wherein said resilient detachable fastener is a stretchable band that engages both said eyeglass lens frame and said sideshield.

13. A full sideshield as in claim 10 wherein one of said sideshields is the mirror image of the other.

14. A full sideshield for attachment to each side of an eyeglass frame as in claim 10 wherein:

said pair of pivotal temples are pivotally attached to said eyeglass lens frame in a spring-loaded fashion to enable movement of said temples in a direction away from each other; and said resilient detachable fastener allows movement of said temples a predetermined distance away from each other.

15. A full sideshield for removable attachment to an eyeglass frame front portion having a pair of spaced eyeglass lens holders, the lens holders having a front and a back and a pair of temples, each temple being attached to a mounting bracket hinge projection extending from a corresponding lens holder for holding the eyeglass frame on the head of a user, said sideshield having an inside and an outside and forming a semicircle around the eyeglass lens holder in front of an eye cavity of the user to provide at least partial eye protection at the top, bottom, and side of the eye, the sideshield comprising:

a generally arcuate-shaped sideshield having a periphery for generally conforming to the shape of the eyeglass lens holder and having a top portion, bottom portion, and a side portion integrally formed as a single unit; and a resilient, detachable fastener for removably and fixedly attaching each sideshield to a respective eyeglass lens holder in a fixed relationship, without movement, as said temples are moved toward each other.

* * * * *

UNITED STATES PATENT AND TRADEMARK OFFICE
CERTIFICATE OF CORRECTION

PATENT NO. : 5,748,278
DATED : May 5, 1998
INVENTOR(S) : Simmons, Sr.

It is certified that error appears in the above-indentified patent and that said Letters Patent is hereby corrected as shown below:

Column 2, line 54, "fall" should read --full--;

Column 9, line 22, "fill" should read --full--;

Column 9, line 40, "sideshield " should read --sideshields--;

Column 10, line 1, "sideshield" should read --sideshields--; and

Column 10, line 1, delete "said" and insert in place thereof --a corresponding--.

Signed and Sealed this

Third Day of November, 1998

Attest:

Attesting Officer

BRUCE LEHMAN

Commissioner of Patents and Trademarks